United States Patent [19]

Slettenmark

[11] Patent Number: 5,758,667
[45] Date of Patent: Jun. 2, 1998

[54] DEVICE FOR LOCATING A PORT ON A MEDICAL IMPLANT

[75] Inventor: Bruno Slettenmark, Jarfalla, Sweden

[73] Assignee: Siemens Elema AB, Solna, Sweden

[21] Appl. No.: 583,657

[22] Filed: Jan. 5, 1996

[30] Foreign Application Priority Data

Jan. 26, 1995 [SE] Sweden .................................. 9500274

[51] Int. Cl.$^6$ .................................................. A61B 19/00
[52] U.S. Cl. .................................................. 128/899
[58] Field of Search .................................. 128/899, 653.1

[56] References Cited

U.S. PATENT DOCUMENTS

| | | | |
|---|---|---|---|
| 4,222,374 | 9/1980 | Sampson et al. | 128/899 |
| 4,784,646 | 11/1988 | Feingold | 604/9 |
| 4,804,054 | 2/1989 | Howosn et al. | 128/898 |
| 5,146,933 | 9/1992 | Boyd | 128/899 |

Primary Examiner—Jennifer Bahr
Assistant Examiner—Eric F. Winakur
Attorney, Agent, or Firm—Hill, Steadman & Simpson

[57] ABSTRACT

A device for locating a port, facing the exterior of a patient, on a medical implant has at least one magnet and a detector arranged to sense magnetic fields. The magnet is associated with the implanted port and the detector is arranged to sense the magnetic field from the outside of the patient's body and, on the basis thereof, determine the location of the port. Alternatively, the detector is associated with the (implanted) port and the magnet is intended to be moved across the area above the detector on the exterior of the patient's body to then determine the location of the port from the magnetic field detected. The device can alternatively use a coil which is associated with the (implanted) port and a ferromagnetic element is moved on the exterior of the patient's body over the area above the coil. Changes in the inductance of the coil when the ferromagnetic means is moved are monitored and, therefrom, the position of the port is identified.

14 Claims, 5 Drawing Sheets

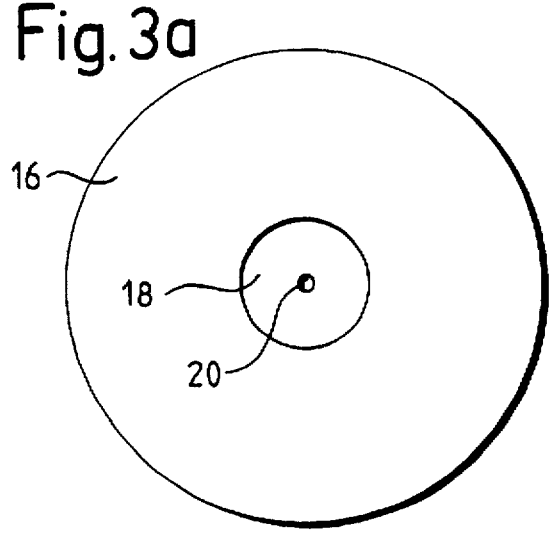
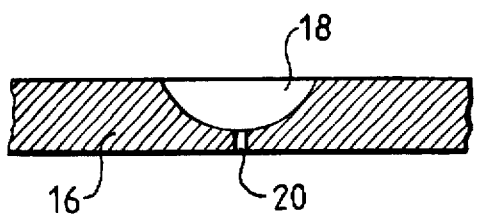
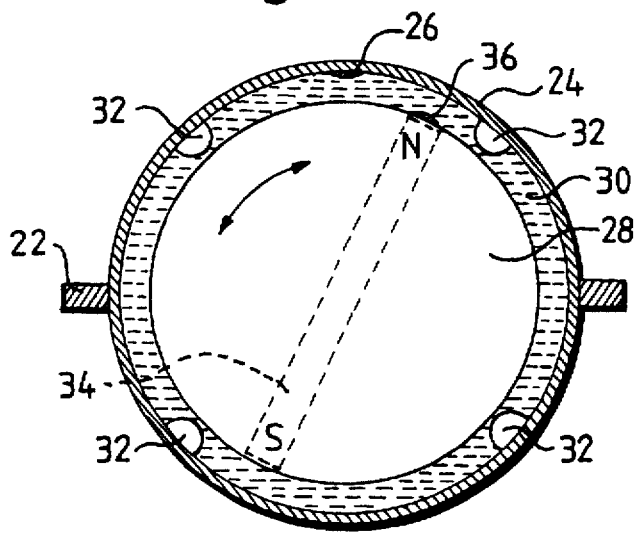
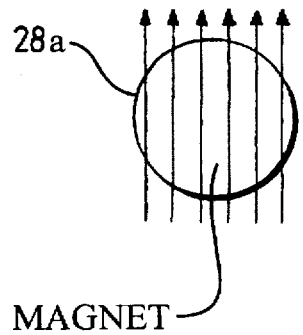

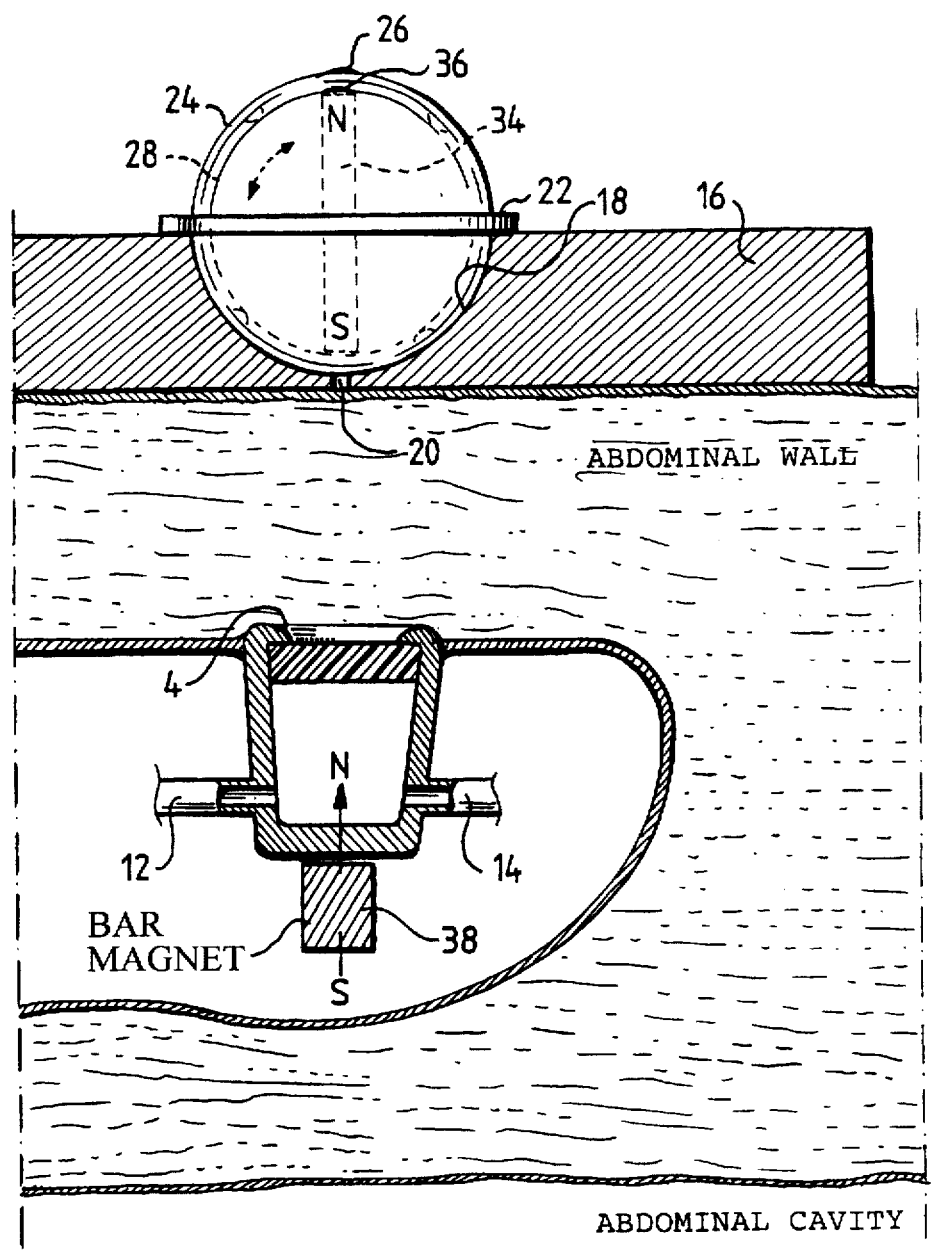

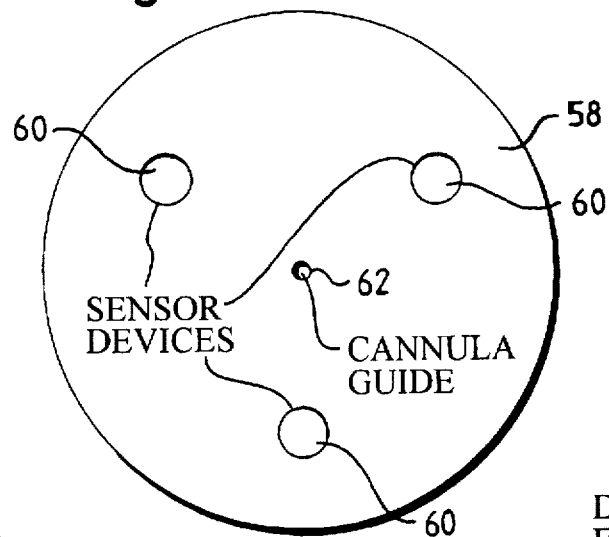
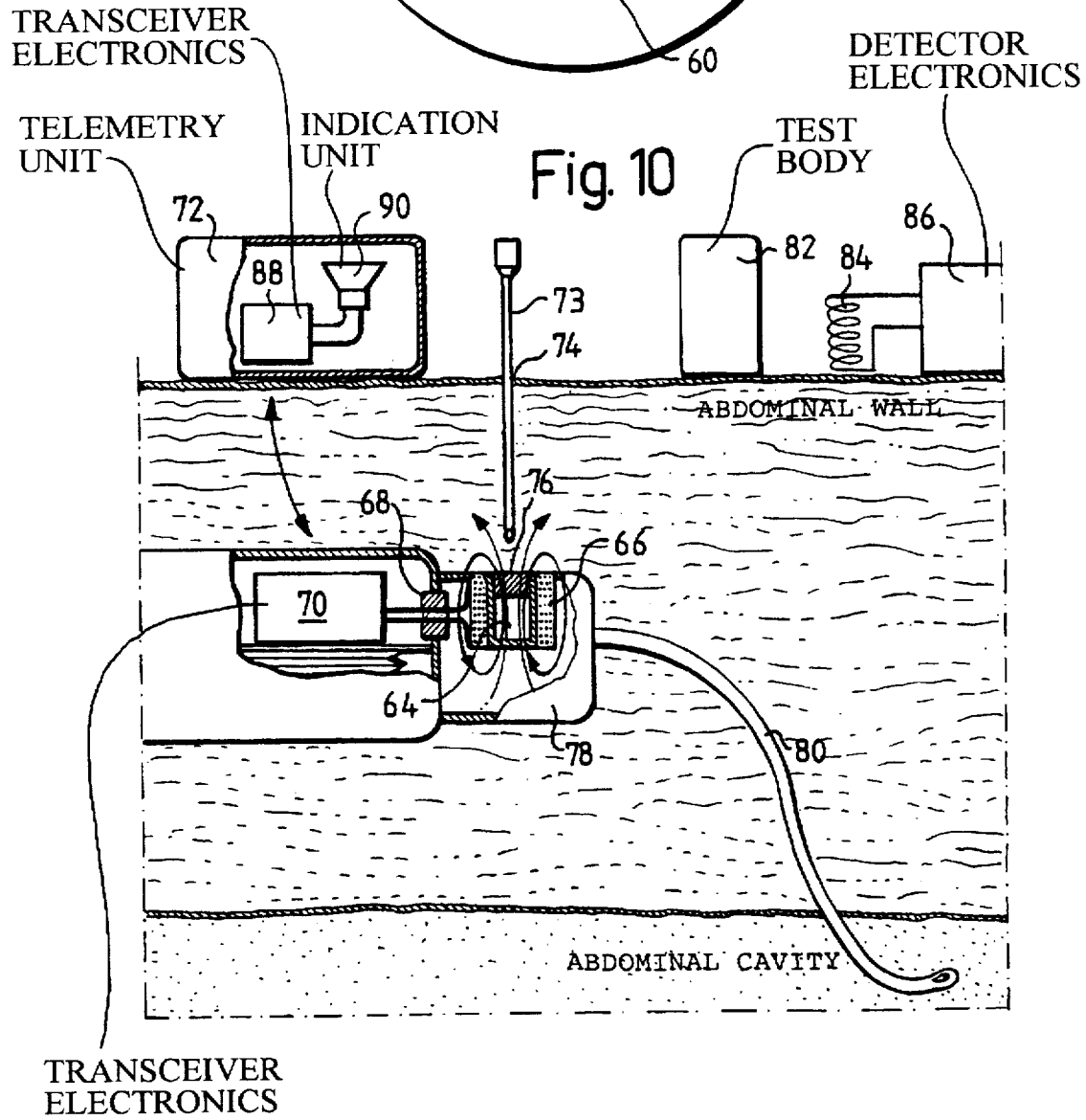

5,758,667

1

DEVICE FOR LOCATING A PORT ON A MEDICAL IMPLANT

BACKGROUND OF THE INVENTION

1. Field of the Invention

The present invention relates to a device for locating a port, facing the exterior of a patient, on a medical implant.

2. Description of the Prior Art

Some medical implants, such as implantable systems for the infusion of liquid medication as shown in FIG. 1, contain ports, viz. a medication filling port 2 and sometimes a so-called flushing port 4, located on the catheter connection 6, for checking and measuring the functioning of the catheter 8 (i.e. whether it is open or occluded etc.), flushing and cleaning the catheter, internal washing and cleaning of the medication container, pump, flushing port etc., for checking pump functions such as stroke volume, backflow etc. and for injecting contrast medium into the catheter for various studies.

The ports are covered by a septum in the form of a rubber membrane. After the device has been implanted in the abdominal wall, the skin and septum can be punctured by a cannula to gain access to the port to refill medication or conduct one of the aforementioned procedures.

Locating the relatively small port, the diameter of which is typically 5 mm, with the tip of the cannula is very difficult. This is especially the case in obese patients in whom finding even the catheter connection molding by palpation may be difficult. The cannula tip is damaged every time the cannula is incorrectly inserted and must be replaced, since a bent cannula tip would damage the septum rubber. This procedure with repeated punctures can be very taxing for both patient and physician, which makes the above-mentioned procedures difficult.

Attempts have been made to facilitate the described procedure by noting the position of the catheter connection on a drawing as a guide in subsequent palpation.

U.S. Pat. No. 4,573,994 discloses a medication infusion apparatus with a funnel-shaped port entrance to facilitate guidance of the cannula tip toward the septum-covered port opening. This patent also shows different ways to confirm that the cannula has reached the correct position in the port.

SUMMARY OF THE INVENTION

An object of the present invention is to solve the aforementioned problems associated with conventional devices and to provide a device for reliably locating the port of a medical implant from the exterior of the patient's body.

The above object is achieved in accordance with the principles of the present invention in a device for locating a port of an implanted medical device which employs two magnetically interacting elements, a first of these magnetically interacting elements being associated with the port at the implanted medical device, such as by surrounding the port, and a second of these magnetically interacting elements being adapted to be moved over the exterior surface of the patient in whom the medical device is implanted. One of the magnetically interacting elements can be a source of a magnetic field and the other of the magnetically interacting elements is then a magnetic field detector. The magnetic field source may be implanted as a part of the medical implant, associated with the port, and then the detector will be the element which is movable over the exterior of the patient. Alternatively, the detector can be implanted with the medical implant and the magnetic field source can be moved over the exterior of the patient. In this alternative, the magnetic field detector will include, or will be connected to, means for providing some type of indicator signal to the exterior of the patient. In another alternative, one magnetically interacting element can be a ferromagnetic element and the other magnetically interacting element will then be an element having an inductance which is alterable dependent on the position of the ferromagnetic element.

In all of these alternative embodiments, the first and second magnetically interacting elements magnetically interact with each other as the second magnetically interacting element is moved over the exterior of the patient, and the magnetic field detector, whether implanted or on the exterior of the patient, provides an extracorporeally perceptible indication when the first and second magnetically interacting units are in a defined spatial relationship, such as the second magnetically interacting element being disposed over the implanted first magnetically interacting unit. The location of the port in the patient is thus identifiable from this extracorporeally perceptible indication. The term "magnetically interact" is used herein in a broad sense, which encompasses inductive interaction.

In the device according to the invention, the relative position of a magnet and a magnetic field detector is thus determined, one of these components being implanted and located at a given position in relation to the port of the implant, whereas the other component is movable on the exterior of the patient's body, and the port of the medical implant is located from the determined relative positions of these components. Alternatively, a coil is implanted in a given position in relation to the port of the implant, and a means, made of a ferromagnetic material, is moved on the exterior of the patient's body over the area of the coil, and from ensuing changes in the inductance of the coil, the relative positions of the coil and the ferromagnetic means, and accordingly the position of the port, can be determined by moving the ferromagnetic means on the exterior of the patient's body.

In one embodiment of the device of the invention, the port is equipped with a rod-shaped magnet, more precisely arranged behind the port along the extension of the central axis of the port. "Centering" the magnet in this way in relation to the port results in greater aiming accuracy when localizing the port.

According to other embodiments of the device of the invention, the detector has a fixture plate, intended to be moved on the patient's skin to locate the port, and an indicator, actuated by the magnetic field and movingly arranged in the fixture plate, designates the position of the port by its position in relation to the fixture plate. The movable plate of the detector has an axially magnetized spherical body which is journaled with low friction in a spherical recess in the plate. When the fixture plate is opposite the port the magnetic body rotates to a given position in the recess. The spherical body is preferably arranged inside a spherical shell with a larger radius than that of the spherical body, the space between the shell and the body being filled at least in part with a liquid to achieve a "suspension" with a minimum of friction. Since the space between the shell and the body is filled with a liquid the density of which is essentially the same as or somewhat higher than that of the spherical body, the spherical body will float in the liquid. The interior of the shell, or the exterior of the spherical body, are also advantageously provided with bumps preventing extended direct surface contact between the spherical body and the shell, thereby avoiding increased friction as a consequence of such a surface contact.

According to another embodiment of the inventive device, a hole is made in the middle of the recess through the fixture plate and a cannula guide is devised to fit in the recess, after the fixture plate has been positioned over the port and the spherical body or the shell has been removed from the recess, the cannula guide being devised to steer a cannula inserted into the guide through the hole in the fixture plate into the port.

According to another embodiment of the device of the invention, at least three indicators, which can be actuated by the magnetic field are movably arranged in the fixture plate, the position of the indicators in relation to the fixture plate designating the position of the port, and the fixture plate further has a cannula guide for guiding a cannula, inserted into the guide, into the port when the fixture plate is in the correct position. This makes it possible to verify continuously that the fixture plate is in the correct position during insertion of the cannula into the port.

In another embodiment of the invention, the cannula has a small diameter along an end section of a given length at the tip and a larger diameter along the rest of the length of the cannula. The end section of the cannula must have a small diameter, so the puncture hole in the port's septum becomes small enough to allow the septum to seal when the cannula is withdrawn. In order to avoid such fine diameter cannulas from being too weak (i.e., too susceptible to bending) they can only be made of limited lengths. This means the cannula will be too short for use with many patients and this problem is accentuated when a fixture plate with a cannula guide is used. Devising only the end section with a small diameter and the rest of cannula with a larger diameter, however, will make cannulas for the most widely ranging abdominal thicknesses stiff enough. Further, the shoulder formed at the location where diameter changes can serve as a stop which prevents the cannula from being inserted too deeply. In this way the risk is eliminated that the cannula tip might hit the bottom of the port and be bent or damaged in some other way, such that the septum is damaged when the cannula is withdrawn.

According to other embodiments of the device of the invention, a coil is wound around the port and is energized by a power source in the implant, the power source being telemetrically controllable from outside the patient. In this way the coil can be conveniently energized only on occasions when a port is to be located, thereby reducing power consumption.

In another embodiment, the unit for determining the change in coil inductance, when a ferromagnetic means on the exterior of the patient's body is moved across the coil area is arranged in the implant, and telemetry equipment is arranged to transmit the determined inductance change to an external received indicator. Thus, the port in question can be located from the outside of the patient's body. The ferromagnetic means can advantageously consist of the cannula, intended to be inserted into the port. The sensed change in induction occurring when the cannula is introduced is then transmitted to the external received indicator, so the insertion of the cannula into the port can be guided with the aid of the received indicator.

DESCRIPTION OF THE DRAWINGS

FIGS. 3a and 3b show a fixture plate at the device according to the invention respectively in a top view and in cross section.

FIG. 4 shows a cross section of a cannula guide for use in the fixture plate in FIG.2.

FIG. 5a shows a spherical body, fitted into the recess of the fixture plate of FIGS. 3a and 3b and with a rod-shaped permanent magnet arranged inside the body.

FIG. 5b shows a solid permanent magnet spherical body for use in the invention.

FIG. 6 illustrates the use of the inventive fixture plate with the spherical body for locating the flushing port of an implanted infusion device, a rod-shaped permanent magnet being arranged behind the port along the extension of the center axis port.

FIG. 9 top view of an alternative embodiment of the fixture plate of the invention.

FIG. 10 illustrates different versions of an embodiment of the invention with a coil arranged around the flushing port of an infusion device.

DESCRIPTION OF THE PREFERRED EMBODIMENTS

Figure 1:
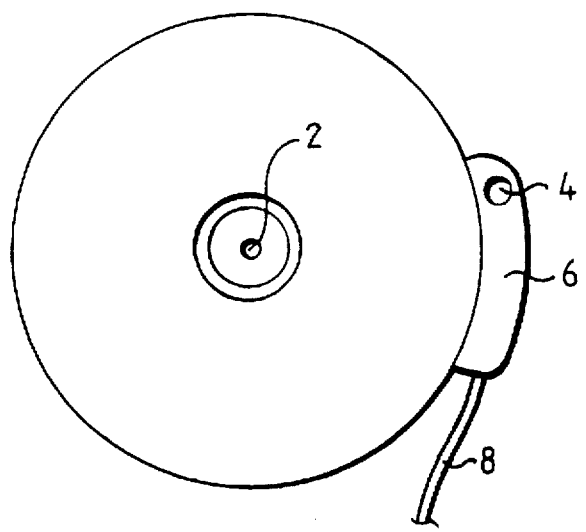
FIG. 1 shows a front view of a conventional medical implant in the form of a system for the infusion of liquid medication.

A device for the infusion of liquid medication, as depicted in FIG. 1, has been described above.

Figure 2A:
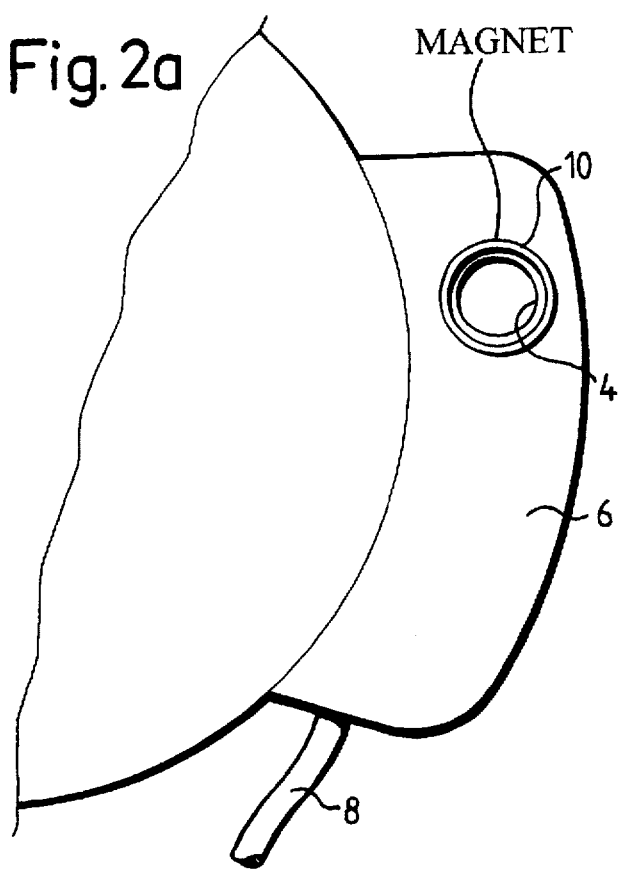
FIG. 2a shows a part of the infusion device in FIG. 1 with a tubular permanent magnet embedded around the flushing port of the device.
Figure 2B:
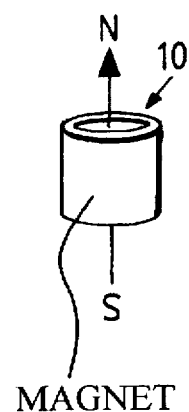
FIG. 2b shows an axially magnetized tube for locating the port when the infusion device is implanted, in accordance with the principles of the present invention.

FIG. 2a shows in larger scale a part of the infusion device in FIG. 1 with the catheter connection 6 and the flushing port 4, around which a permanent magnet in the form of a tube 10 is embedded in accordance with the invention. The tubular magnet 10 is axially magnetized, (see FIG. 2b), and has high coercive force and a high energy product. A large magnetic moment is desirable for obtaining the best axial field distribution.

Recesses are provided in the magnet for input and output tubes 12 and 14 to and from the flushing port 4, (see FIG. 6).

As an alternative, a rod-shaped permanent magnet can be 5 arranged coaxially with the port 4 and behind the same along an extension of the center axis of the port 4, (see FIG. 6).

The port 4 itself, as well as the enclosure of the device and other adjacent materials, should be non-magnetic, e.g. made 10 of titanium or epoxy plastic.

FIGS. 3a and 3b show a fixture plate 16 with a central, hemispherical recess 18 with a small hole 20 in the middle.

FIG. 5a shows a spherical device, fitted into the recess 18 in the fixture plate 16. For localizing the flushing port 4, equipped with a magnet, the spherical device is placed in the recess 18 with an equatorial plate 22, arranged on the device, bearing against the upper side of the fixture plate 16.

The spherical device has an external shell 24, at least the upper half of which is transparent and has a central marking 26, in the form of a cross or the like, on its top.

A spherical body 28 is mounted inside the outer shell 24 with the lowest possible friction. This is appropriately achieved by completely or partly filling the space 30 between the outer shell 24 and the spherical body 28 with a liquid. The center of gravity of the spherical body 28 should be located as centrally as possible to prevent undesirable torques. The resulting density of the spherical body 28 is preferably equal to or almost equal to the density of the liquid in the space 30. The spherical body 28 will then float in the liquid with extremely low friction, and the absence of air and/or a liquid meniscus will eliminate undesirable surface tension forces.

Alternatively, the spherical body 28 can be devised in such a way that its resulting density is less than the density of the liquid. The space 30 is then filled to such a degree that 5 the spherical body 28 floats centrally in the outer shell 24.

In both the above described embodiments, a number of "bumps" 32, i.e., at least four, can be arranged on the inner side of the outer shell 24, or on the outer side of the spherical body 28, to avoid extended surface contact and, accordingly, increased friction, between the spherical body 28 and the shell 24.

The spherical body 28 can be made of a non-magnetic material 15 with a permanently magnetized bar magnet 34 arranged along a diameter (see FIG. 5a). The surface of the spherical body 28 is provided with a visible marking 36 at its north pole.

As an alternative to the above described version, the 20 spherical body can be a solid, axially magnetized permanent magnet 28a, as shown in FIG. 5b.

As an alternative to the above described "frictionless" suspensions of the spherical body 28, other known principles for suspending principles for suspending a bar magnet with a central pivoting point, coinciding with the center of gravity of the magnet and with two angular degrees of freedom inside the outer shell, can be used, since rotation around the axis of the bar magnet is unnecessary. As an example some form of gyro suspension of the bar magnet can be used, the spherical body itself then not being needed. The spherical outer shell, however, can be filled with liquid for damping and/or lubricating the mechanical system, if desired.

Locating the port with the device according to the invention is performed as follows:

The patient with the implant in his or her abdomen is placed on his or her back, and the fixture plate 16 is positioned with its center in the vicinity of the anticipated location of the port. The plate 16 has a comparatively large diameter for stable placement on the skin of the patient's abdomen. The spherical sensor device is inserted into the recess 18 in the plate 16 with the equatorial plate 22 bearing against the upper side of the fixture plate, as shown in FIG. 6. The fixture plate is moved laterally on the abdomen, the magnet 34 being acted on by the magnetic field from the magnet 38 at the port 4, and as the mark 36 at the north pole of the magnet 34 becomes aligned with the marking 26 on the outer shell 24, the fixture plate 16 becomes situated opposite the port 4, and it is immobilized in this position. The spherical sensor device is then lifted out of the recess 18 and is replaced with the cannula guide 40 shown in FIG. 4. The cannula guide 40 fits in the recess 18 with the channel 42 aligned with the hole 20 in the fixture plate 16. A cannula 44 can then be passed through the channel 42 and hole 20 into the port 4, the fixture plate 16 with the cannula guide 40 then serving as an aiming means, as shown in FIG. 7.

Figure 7:
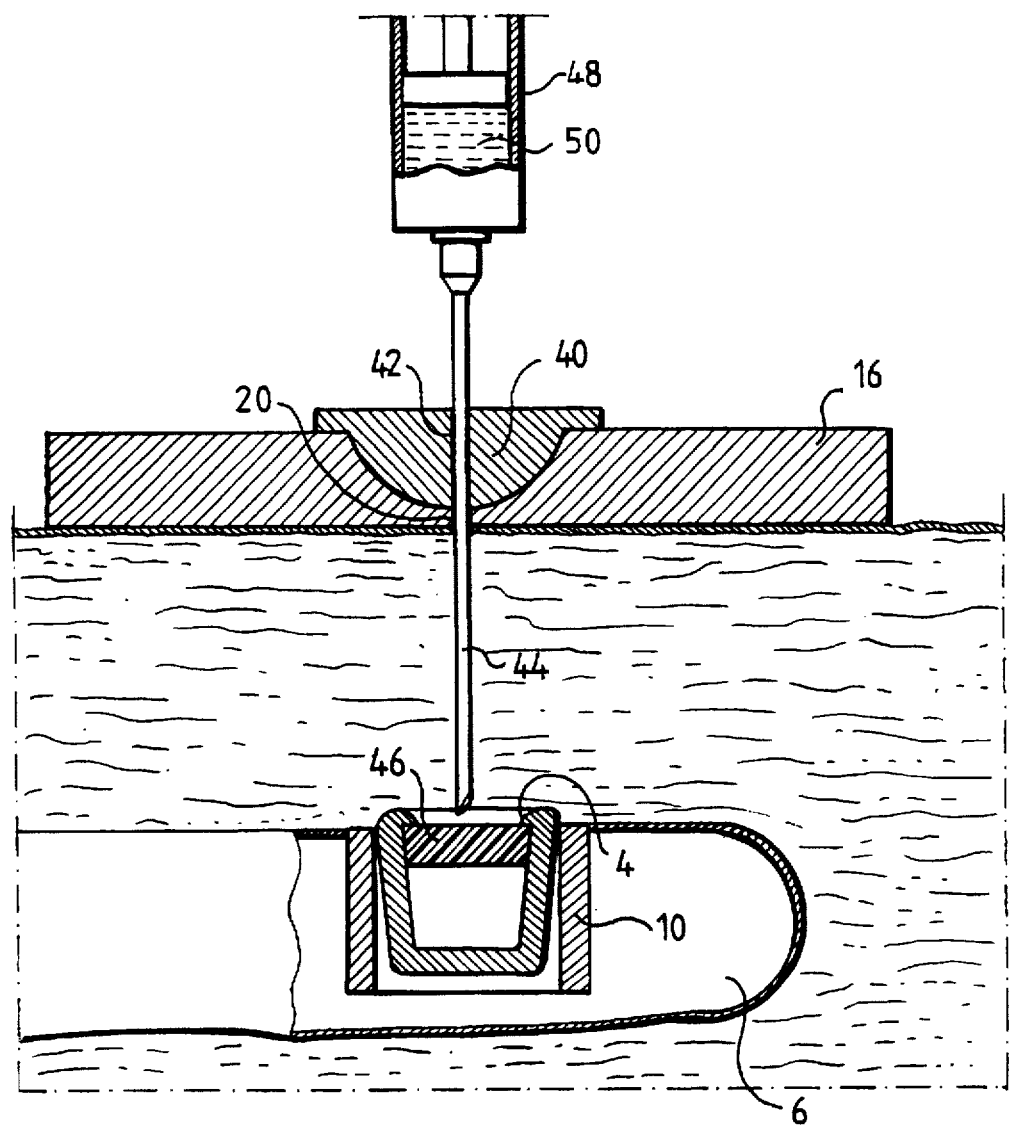
FIG. 7 shows the introduction of the cannula into the flushing port with the aid of the cannula guide in the inventive fixture plate.

In the embodiment shown in FIG. 7, the port 4 is encircled by the tubular magnet 10, and the port 4 itself is covered by a rubber septum 46 which is penetrated by the cannula 44.

The cannula 44 is further connected to a syringe 48 containing the liquid 50 injected into the port after the cannula 44 has been introduced.

As an alternative to the use of the cannula guide 40, a marking can simply be made on the patient's skin with a suitable pen through the hole 20 in the base of the fixture plate 16 after the sensor device has been removed. The 35 fixture plate 16 is then removed, and the cannula 44 can be inserted perpendicularly to the skin at the marking.

The earth's magnetic field is negligible, compared to the near field of the permanent magnet. It is desirable, however, that strong sources of interference, such as electromagnets, other permanent magnets, soft iron etc., be avoided in the vicinity of the sensor device in order to reduce undesirable deviations.

Figure 8:
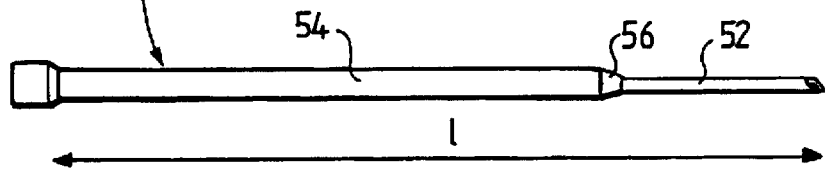
FIG. 8 shows an embodiment of a cannula, suitable for introduction into a port of the implant with the aid of a fixture plate in accordance with the invention.

The cannula 44 which is used must have a small diameter to prevent damage to the septum 46. The cannula 44 will therefore be weak and can only be made in limited lengths. Currently employed cannulas are therefore rather short for many patients and the problems with short cannulas are accentuated when using a fixture plate 16 with cannula guide 40. It is therefore advantageous to devise the cannula in the way shown in FIG. 8. The end section 52 of this cannula has a small diameter to only make a tiny puncture hole in the septum. The length of this end section 52 is limited, typically 7 to 8 mm. The remainder 54 of the cannula has a larger diameter, enabling the cannula to be made long enough to suit most varying abdominal thicknesses while maintaining sufficient stiffness. Another advantage with this design of the cannula is that a shoulder, blocking further penetration of the septum by the cannula, is formed at the diameter change junction 56 of the cannula. In this way it can be avoided that the tip of the cannula strikes the bottom of the port 4, which is an important advantage since the cannula tip would be bent if it is pressed against the bottom of the port 4. A bent cannula tip would then damage the septum rubber when the cannula is withdrawn from the port 4.

FIG. 9 shows an alternative embodiment of a fixture plate 58 with three sensor devices 60 of the above described kind. The sensor devices 60 are symmetrically arranged around the 35 center of the fixture plate 58 where a channel 62 is formed perpendicularly through the plate 58.

With the aid of the sensor devices 60, the plate 58 can be positioned exactly over the port, equipped with a magnet, so the channel 62 is right over the port in a manner analogous to that described above, whereupon a cannula can be introduced through the channel 62 and into the underlying port, the channel 62 thus serving as an aiming means.

In this embodiment, the sensor devices 60 do not have to be removed from the fixture plate 58 when the cannula is introduced through the guide channel 62. The sensor devices 60 can therefore be permanently mounted in the fixture plate 58, and checks can be made, throughout the process of introducing the cannula into the port and injecting liquid, to ensure that the fixture plate 58 is in the correct position in relation to the port.

FIG. 10 shows another alternative embodiment of the device according to the invention in which the flushing port 64 is made of a non-ferromagnetic metal and is encircled by a coil 66. The winding of the coil is connected, via a hermetically sealed two-pin terminal block 68, to transceiver electronics 70 in the hermetically sealed electronics compartment of the infusion device. The transceiver electronics 70 can be activated by a 25 telemetry unit 72 placed on the patient's abdomen above the implant to deliver a weak alternating current at an appropriate frequency through the coil 66.

The cannula 73 which is to be introduced into the flushing 30 port 64 via the port's septum 76 is inserted through the skin at an appropriate point 74.

Conventionally, the appropriate point 74 can be located by palpation of the molding for the connection 78 for the catheter 80. This palpation 35 may be difficult on obese patients. Alternately, the surgeon can make a mark, e.g. a small tatoo or the like, on the patient's skin immediately above the port at the time of implantation of the infusion device.

A better and more accurate technique according to the present invention is achieved by placing a ferromagnetic test body 82 on the patient's skin. This body 82 affects the inductance of the coil 66, and this effect is a function of the distance to and angle in relation to the coil axis. The maximum effect on the coil inductance is achieved when the test body 82 is situated immediately above the flushing port, provided the axis of the coil is reasonably perpendicular to the plane of the abdomen.

An alternative according to the invention for locating the correct position for inserting the cannula into the patient is to sense the alternating field from the coil 66 of the flushing port 64 with the aid of a detector coil 84 and attendant detector electronics 86. A maximum signal is obtained from the detector coil 84 when it is in a position on the abdomen which is coaxial to the coil 66 of the flushing port 64.

Another alternative according to the invention is to use a cannula 73 made of a ferromagnetic material. When the cannula 73 then is inserted into the abdominal wall at the point 74 and approaches the flushing port 64, the inductance of the coil an increases, an increase detectable with the electronics unit 70.

The change in inductance can be detected e.g. as a change in current, a change in phase angle or a change in the resonance frequency of a tuned LC circuit. The change in the actual parameter is transmitted by telemetry to the transceiver electronics 88 in the telemetry unit 72 and is presented with appropriate indication unit 90, such as an acoustic signal generator, optical signal generator or the like. Thus, the indicating unit 90 can be arranged to emit e.g. an acoustic signal whose strength, or frequency, is proportional to the inductance of the coil 66. As the tip of the cannula comes closer to the flushing port 64, the signal becomes stronger or, alternatively, the frequency of the sound becomes higher. Alternatively, the indication unit 90 can be a lamp, light-emitting diode or the like which blinks at a varying rate depending on the proximity of the cannula 73 to the port 84.

By utilizing feedback obtained via the indication unit 90, the operator can slowly advance the cannula 73 toward the port 64 and steer it accurately until the cannula 73 hits the flushing port 64.

When the cannula 73 has reached the correct position in the 15 flushing port 64, the electronics 70 are deactivated by a telemetry signal from the unit 72 in order to save energy in the battery of the implant.

In the above described manner, the presence of the cannula 73 in the port 64 can thus be sensed inductively. Thus, the correct position of the cannula 73 can be verified throughout the entire flushing operation. Verifying that the cannula is in the correct position in the port in question is particularly important when implanted infusion devices are filled with medication, such as insulin. According to the above, a similar device can be consequently be employed to ensure that the cannula remains in the filling port 2 in FIG. 1 throughout the filling operation, so insulin is not injected at an erroneous site because the cannula slips out of the filling port.

The above described technique according to the invention can also be applied to standard cannulas made of non-ferromagnetic materials. Eddy currents and losses in non-ferromagnetic metals cause a detectable reduction in inductance, a phase shift in the current etc. The effect is less pronounced, however, than when a cannula made of a ferromagnetic material is used. Moreover, the coil-encircled port in this instance is made of metal which reduces sensitivity to the position of the cannula. This difficulty will be eliminated if the metallic material, such as polymer, ceramic or the like.

All the components in the device according to the invention are advantageously made of materials and are devised in a way enabling them to be sterilized with normal methods.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device, for use with a medical implant having a port, for locating the port after implantation of said medical implant in a patient, said device comprising:

a magnetic field source adapted to be disposed in a patient in whom said medical implant is implanted at a known spatial position relative to said port;

a fixture plate movable across the skin of the patient, said fixture plate having a hemispherical recess therein; and indicator means, movably mounted in said fixture plate and positionally responsive to a magnetic field from said magnetic field source, for providing an extracorporeally perceptible indication when said fixture plate is in a defined spatial relationship to said magnetic field source for extracorporeally identifying a position of said port in said patient, said indicator means comprising an axially magnetized spherical body mounted in said recess for substantially free rotation therein, said axially magnetized spherical body having a marking thereon identifying the position of said spherical body relative to said fixture plate.

2. A device as claimed in claim 1 wherein said magnetic field source comprises an axially permanently magnetized tube adapted to be disposed surrounding said port.

3. A device as claimed in claim 2 wherein said port has at least one tube communicating therewith, and wherein said axially permanently magnetized tube comprises a recess adapted for receiving said at least one tube therethrough.

4. A device claimed in claim 1 wherein said port has a center axis, and wherein said magnetic field source comprises a bar-magnet adapted to be disposed behind said port with said port between said bar magnet and the exterior of the patient, and having poles aligned with said center axis of said port.

5. A device as claimed in claim 1 wherein said spherical body is magnetized in a same direction throughout its volume.

6. A device as claimed in claim 1 wherein said spherical body comprises a spherical body of non-magnetic material with a permanent bar magnet disposed along a diameter of said non-magnetic spherical body.

7. A device as claimed in claim 1 further comprising a spherical shell mounted on said fixture plate in which said spherical body is disposed, said spherical shell having an inner radius which is larger than a radius of said spherical body so that a space exists between said spherical body and an interior of said spherical shell, and said space being filled with a liquid.

8. A device as claimed in claim 7 wherein said spherical body has a density, and wherein said liquid has a density not less than said density of said spherical body.

9. A device as claimed in claim 7 wherein said spherical body has a density, and wherein said liquid has a density substantially higher than said density of said physical body for causing said spherical body to float substantially centrally in said interior of said spherical shell.

10. A device as claimed in claim 7 wherein said spherical body has a plurality of projections extending therefrom for preventing extended surface contact between said spherical body and the interior of said spherical shell.

11. A device as claimed in claim 7 wherein said spherical shell has a plurality of inwardly extending projections therein for preventing extended surface contact between said spherical body and the interior of said spherical shell.

12. A device as claimed in claim 7 wherein said spherical shell has an upper half which is transparent and having a centrally disposed first mark at a top of said upper half, and wherein said spherical body has a second mark thereon, said fixture plate being disposed opposite said port when said first and second marks are aligned.

13. A device, for use with a medical implant having a port, for locating the port after implantation of said medical implant in a patient, said device comprising:

a magnetic field source adapted to be disposed in a patient in whom said medical implant is implanted at a known spatial position relative to said port;

a fixture plate movable across the skin of the patient, said fixture plate having an opening therein;

indicator means, movably mounted in said fixture plate and positionally responsive to a magnetic field from said magnetic field source, for providing an extracorporeally perceptible indication when said fixture plate is in a defined spatial relationship to said magnetic field source for extracorporeally identifying a position of said port in said patient;

a holder for said indicator means removably disposed in said opening; and a cannula guide fittable into said opening upon removal of said indicator means after locating the position of said port.

14. A device as claimed in claim 13 further comprising a cannula insertable through said cannula guide, said cannula having a small diameter end portion and a remainder having a larger diameter than said small diameter end portion.

* * * * *